(12) United States Patent
Koele et al.

(10) Patent No.: US 7,935,296 B2
(45) Date of Patent: May 3, 2011

(54) PROCESS FOR THE DETECTION OF MARKED COMPONENTS OF A COMPOSITE ARTICLE USING INFRARED BLOCKERS

(75) Inventors: Matthew L. Koele, Chilton, WI (US); Clinton D. Clark, Reno, TX (US); Jerome J. Workman, Jr., Brookline, MA (US); Kent A. Franklin, Appleton, WI (US); Thomas M. Flicker, Neenah, WI (US); Bradley M. Marohl, Neenah, WI (US); Joseph J. Gimenez, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1202 days.

(21) Appl. No.: 11/037,478

(22) Filed: Jan. 18, 2005

(65) Prior Publication Data
US 2005/0122531 A1 Jun. 9, 2005

Related U.S. Application Data

(62) Division of application No. 10/210,685, filed on Jul. 31, 2002, now Pat. No. 6,927,857.

(60) Provisional application No. 60/362,833, filed on Mar. 9, 2002, provisional application No. 60/372,866, filed on Mar. 9, 2002, provisional application No. 60/364,264, filed on Mar. 14, 2002, provisional application No. 60/364,329, filed on Mar. 14, 2002, provisional application No. 60/382,812, filed on May 23, 2002.

(51) Int. Cl.
*G01B 15/00* (2006.01)

(52) U.S. Cl. .................................................. 264/410
(58) Field of Classification Search .................. 264/410, 264/437; 252/645; 235/468
See application file for complete search history.

(56) References Cited

U.S. PATENT DOCUMENTS

| | | | |
|---|---|---|---|
| 2,935,559 A | 5/1960 | Domier | |
| 2,984,699 A | 5/1961 | Domier | |
| 3,711,176 A | 1/1973 | Alfrey, Jr. et al. | |
| 4,166,541 A | 9/1979 | Smith, Jr. | |
| 4,170,419 A | 10/1979 | Van Tyne et al. | |
| 4,543,141 A | 9/1985 | Bradley et al. | |

(Continued)

FOREIGN PATENT DOCUMENTS
EP     0 043 723 A2    1/1982
(Continued)

OTHER PUBLICATIONS
International Search Report for PCT/US 03/06073 dated Jul. 2, 2003.
(Continued)

*Primary Examiner* — Christina Johnson
*Assistant Examiner* — Galen Hauth
(74) *Attorney, Agent, or Firm* — Armstrong Teasdale LLP (57) ABSTRACT

Disclosed is a process for the detection of marked components of a composite article. The present invention relates to detecting the presence, position, concentration and/or distribution of one or more components in a composite article, and to registration inspection of a composite article using infrared radiation. In one embodiment of the invention, infrared blockers, such as absorbing infrared blockers, are incorporated into the component of interest in the composite to increase the visibility of the marked component during inspection.

17 Claims, 6 Drawing Sheets

U.S. PATENT DOCUMENTS

| | | | |
|---|---|---|---|
| 4,614,969 | A | 9/1986 | Gerundt et al. |
| 4,663,220 | A | 5/1987 | Wisneski et al. |
| 4,680,205 | A | 7/1987 | Lerner et al. |
| 4,685,475 | A | 8/1987 | Ridler et al. |
| 4,704,116 | A | 11/1987 | Enloe |
| 4,806,776 | A | 2/1989 | Kley |
| 4,811,002 | A | 3/1989 | Otsubo |
| 4,837,715 | A | 6/1989 | Ungpiyakul et al. |
| 4,877,940 | A | 10/1989 | Bangs et al. |
| 4,900,382 | A | 2/1990 | Klose |
| 4,940,464 | A | 7/1990 | Van Gompel et al. |
| 4,972,093 | A | 11/1990 | Cochran et al. |
| 4,982,103 | A | 1/1991 | Meiffren et al. |
| 5,045,135 | A | 9/1991 | Meissner et al. |
| 5,046,272 | A | 9/1991 | Vogt et al. |
| 5,103,337 | A | 4/1992 | Schrenk et al. |
| 5,104,116 | A | 4/1992 | Pohjola |
| 5,110,403 | A | 5/1992 | Ehlert |
| 5,166,536 | A | 11/1992 | Rye |
| 5,182,722 | A | 1/1993 | Hain |
| 5,204,538 | A | 4/1993 | Genovese |
| 5,224,405 | A | 7/1993 | Pohjola |
| 5,226,992 | A | 7/1993 | Morman |
| 5,235,515 | A | 8/1993 | Ungpiyakul et al. |
| 5,246,433 | A | 9/1993 | Hasse et al. |
| 5,286,543 | A | 2/1994 | Ungpiyakul et al. |
| 5,343,049 | A | 8/1994 | Vareille et al. |
| 5,347,135 | A | 9/1994 | Harris et al. |
| 5,359,525 | A * | 10/1994 | Weyenberg ............ 700/124 |
| 5,399,016 | A | 3/1995 | Martin |
| 5,483,893 | A | 1/1996 | Isaac et al. |
| 5,500,063 | A | 3/1996 | Jessup |
| 5,547,531 | A | 8/1996 | Allen et al. |
| 5,549,537 | A | 8/1996 | Focke et al. |
| 5,552,007 | A | 9/1996 | Rajala et al. |
| 5,626,711 | A | 5/1997 | Herrmann |
| 5,635,724 | A | 6/1997 | Higgins |
| 5,637,864 | A | 6/1997 | Nicks et al. |
| 5,644,140 | A | 7/1997 | Biedermann et al. |
| 5,660,666 | A | 8/1997 | Dilnik et al. |
| 5,663,565 | A | 9/1997 | Taylor |
| 5,726,758 | A | 3/1998 | Hasegawa et al. |
| 5,755,902 | A | 5/1998 | Reynolds |
| 5,766,389 | A | 6/1998 | Brandon et al. |
| 5,772,825 | A | 6/1998 | Schmitz |
| 5,779,831 | A | 7/1998 | Schmitz |
| 5,818,719 | A | 10/1998 | Brandon et al. |
| 5,855,574 | A | 1/1999 | Kling et al. |
| 5,858,515 | A | 1/1999 | Stokes et al. |
| 5,870,203 | A | 2/1999 | Chiu et al. |
| 5,879,500 | A | 3/1999 | Herrin et al. |
| 5,930,139 | A | 7/1999 | Chapdelaine et al. |
| 5,980,087 | A | 11/1999 | Brandon et al. |
| 6,040,903 | A | 3/2000 | Lysen et al. |
| 6,067,155 | A | 5/2000 | Ringlien |
| 6,082,732 | A | 7/2000 | Hutchison et al. |
| 6,092,002 | A | 7/2000 | Kastman et al. |
| 6,166,393 | A | 12/2000 | Paul et al. |
| 6,198,102 | B1 | 3/2001 | Shepherd |
| 6,217,794 | B1 | 4/2001 | Neal et al. |
| 6,224,699 | B1 | 5/2001 | Bett et al. |
| 6,245,168 | B1 | 6/2001 | Coenen et al. |
| 6,253,159 | B1 | 6/2001 | Bett et al. |
| 6,259,526 | B1 | 7/2001 | Pace et al. |
| 6,270,599 | B1 | 8/2001 | Wood |
| 6,323,954 | B1 | 11/2001 | Halter |
| 6,335,094 | B1 * | 1/2002 | Owaki et al. ............ 428/374 |
| 6,352,497 | B1 | 3/2002 | Hensley et al. |
| 6,444,064 | B1 | 9/2002 | Henry et al. |
| 6,651,894 | B2 * | 11/2003 | Nimura et al. ............ 235/494 |
| 2001/0016059 | A1 | 8/2001 | Krahn et al. |
| 2002/0000291 | A1 | 1/2002 | Coenen et al. |
| 2002/0055430 | A1 | 5/2002 | Coenen et al. |

FOREIGN PATENT DOCUMENTS

| | | |
|---|---|---|
| EP | 0 217 032 A3 | 8/1987 |
| EP | 0 217 032 B1 | 8/1987 |
| EP | 0 320 991 A2 | 6/1989 |
| EP | 0 328 890 A1 | 8/1989 |
| EP | 0 554 911 A1 | 8/1993 |
| WO | WO 96/17303 A1 | 6/1996 |
| WO | WO 96/19346 A2 | 6/1996 |
| WO | WO 96/19347 A2 | 6/1996 |
| WO | WO 99/36809 A1 | 7/1999 |
| WO | WO 99/36810 A1 | 7/1999 |
| WO | WO 00/37009 A2 | 6/2000 |
| WO | WO 00/40196 A1 | 7/2000 |
| WO | WO 00/45767 A1 | 8/2000 |
| WO | WO 01/83347 A1 | 11/2001 |
| WO | WO 01/87210 A1 | 11/2001 |
| WO | WO 01/87211 A2 | 11/2001 |
| WO | WO 01/87211 A3 | 11/2001 |
| WO | WO 01/87218 A2 | 11/2001 |
| WO | WO 01/87562 A2 | 11/2001 |
| WO | WO 01/87753 A2 | 11/2001 |
| WO | WO 01/87753 A3 | 11/2001 |

OTHER PUBLICATIONS

International Search Report, PCT/US 03/06074 dated Aug. 13, 2003, 4 pages.

International Search Report, PCT/US 03/06128, from the European Patent Office dated Aug. 1, 2003.

International Search Report, PCT/US 03/06148, from European Patent Office dated Aug. 8, 2003.

* cited by examiner

PROCESS FOR THE DETECTION OF MARKED COMPONENTS OF A COMPOSITE ARTICLE USING INFRARED BLOCKERS

CROSS-REFERENCE TO RELATED APPLICATIONS

This application is a divisional of Ser. No. 10/210,685, filed Jul. 31, 2002 which claims the benefit of provisional application Ser. No. 60/362,833, filed Mar. 9, 2002, provisional application Ser. No. 60/372,866, filed Mar. 9, 2002, provisional application Ser. No. 60/364,264, filed Mar. 14, 2002, provisional application Ser. No. 60/364,329, filed Mar. 14, 2002, and of provisional application Ser. No. 60/382,812, filed May 23, 2002, all of which are hereby incorporated by reference in their entirety for all purposes.

FIELD OF THE INVENTION

The present invention relates to detecting the presence, position, concentration and/or distribution of one or more components in a composite article, and to registration inspection of a composite article, using infrared radiation and infrared detectors in conjunction with the addition of an infrared blocker to the components.

BACKGROUND OF THE INVENTION

A vast number of applications exist in which it is necessary or desirable to monitor the presence and/or position of one or more components of a composite article during manufacturing. For instance, in a largely automated process for manufacturing disposable absorbent products such as diapers and other incontinence products, certain components (e.g., support layers, absorbent pads, elastic components, fastener components, etc.) must be positioned or aligned with respect to each other and/or other components in order to produce an acceptable product. Accordingly, inspection systems are commonly used to detect the positions of such components during manufacturing. If an inspection system determines that one or more components are out of position and thus do not properly register with other components, the inspection system typically outputs one or more signals indicating that certain articles should be culled and discarded, that the process should be adjusted so as to bring out-of-position components into proper position, that the process should be adjusted so that subsequent components are brought into proper registration with one another, etc.

An exemplary registration inspection system is disclosed in U.S. Pat. No. 5,359,525, the disclosure of which is incorporated herein by reference. As described therein, registration inspection of a composite article undergoing fabrication is accomplished by producing an image of the article and then analyzing the image to detect the position of one or more components. The detected positions are then compared to ideal positions to thereby determine whether the one or more components are properly positioned. This registration inspection system employs conventional video cameras for capturing visible and ultraviolet light reflected by and/or transmitted through components in order to produce still video images of such components. Thus, after producing a video image of a composite article and its several components, the image can be analyzed to determine whether the components are properly positioned and registered with one another.

Although highly useful for many applications, the inventors hereof have determined that the inspection system disclosed in the aforementioned patent, and similar systems, have certain shortcomings. For example, such systems are not well suited for determining the presence and/or positions of components underlying other components which are substantially opaque to visible and/or ultraviolet light. Additionally, such systems are not well suited to determining the presence and/or positions of components which tend to scatter visible and ultraviolet light.

Another exemplary inspection system, disclosed in U.S. Pat. No. 6,224,699, employs infrared detectors for producing infrared images of products undergoing formation by sensing infrared radiation emitted by heated product components. The produced images are then compared with reference information to determine, for example, whether the product components are properly positioned. However, this system is not well suited to detecting product components which have cooled, or which were never heated in the first instance.

The inventors hereof have also recognized that prior art inspection systems and processes are not well suited to detecting the distribution and/or concentration level (e.g., quantity) of certain product components.

SUMMARY OF THE INVENTION

In order to solve these and other needs in the art, the inventors hereof have succeeded at designing processes and systems for detecting the presence, position, distribution and/or concentration of one or more components in a composite article, including adjacent components, overlapping components, and components which overlie or underlie other components, including components which are disposed or sandwiched between other components. The present invention also relates to composite articles produced or inspected using such processes and systems. The invention is especially well suited to detecting properties of disposable absorbent articles undergoing fabrication and/or quality inspection, although the invention is far from so limited, as will be apparent from the description below.

BRIEF DESCRIPTION OF THE DRAWINGS

FIGS. 3($a$) and 3($b$) are side and top views of an exemplary composite article.

FIG. 3($c$) illustrates an image of the composite article of FIGS. 3($a$) and 3($b$) produced using the system of FIG. 2.

Corresponding reference characters indicate corresponding features throughout the several views of the drawings.

DETAILED DESCRIPTION OF PREFERRED EMBODIMENTS

A. Infrared Registration Inspection System

Figure 1:
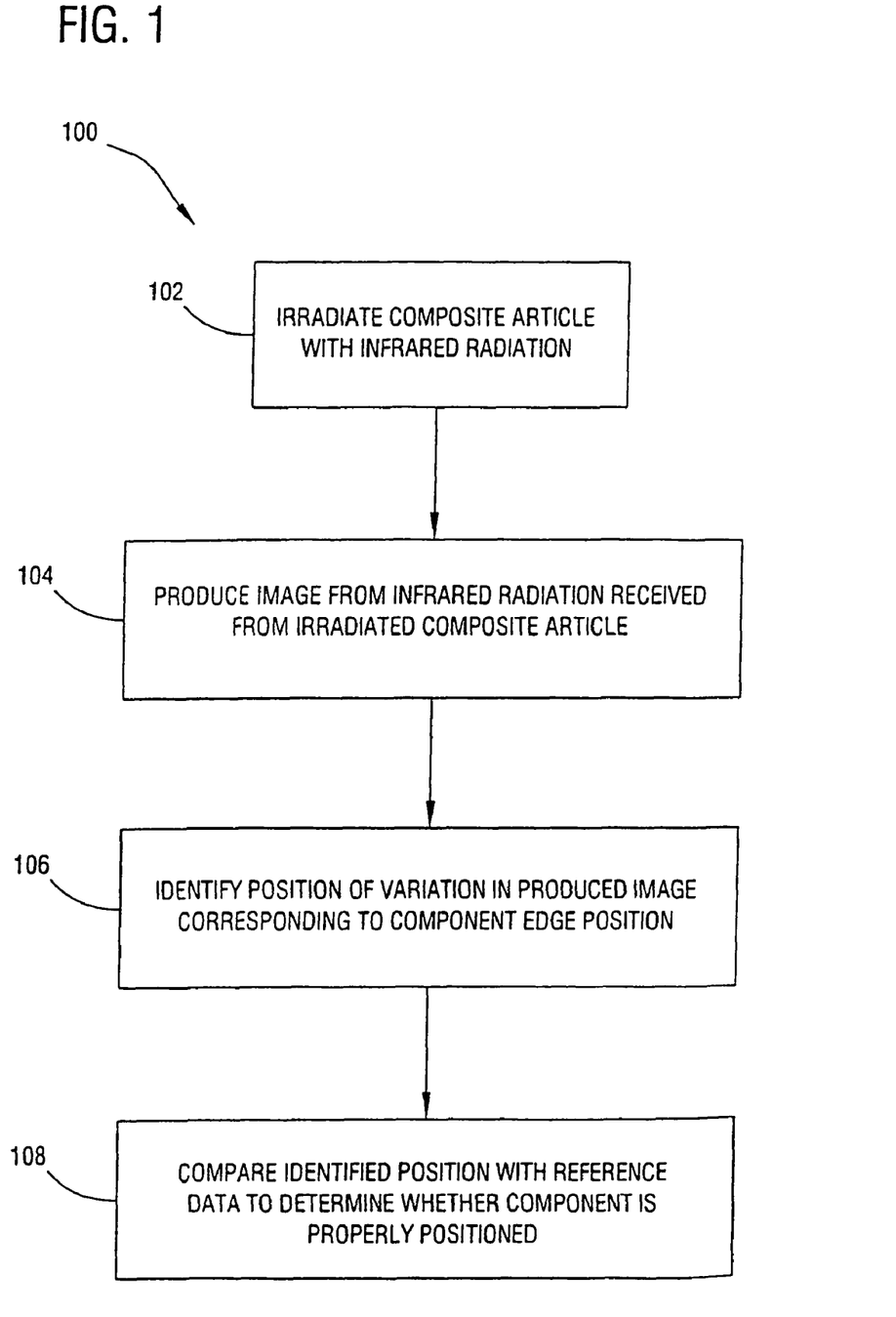
FIG. 1 is a flow diagram of a process for detecting whether one or more components are properly positioned in a composite article according to one preferred embodiment of the present invention.

A process of detecting whether one or more components are properly positioned in a composite article is illustrated in FIG. 1 and indicated generally by reference character 100. The process 100 includes irradiating the composite article with infrared radiation as shown in block 102 of FIG. 1, and producing an image from infrared radiation received from the irradiated composite article, as shown in block 104. The process further includes, in block 106, identifying a position of a variation in the produced image corresponding to an edge position of a component in the composite article. In block 108, the position of the variation identified in the produced image (in block 106) is compared with reference data to thereby determine whether the component of the composite article is properly positioned therein. By utilizing infrared radiation rather than (or in addition to) visible light, the process 100 cannot only detect the position of components which tend to scatter visible and ultraviolet light, including components which overlie other components, but also the position of components which underlie other components, including components disposed or sandwiched between components which are substantially opaque to visible and ultraviolet light, as further explained below.

Figure 2:
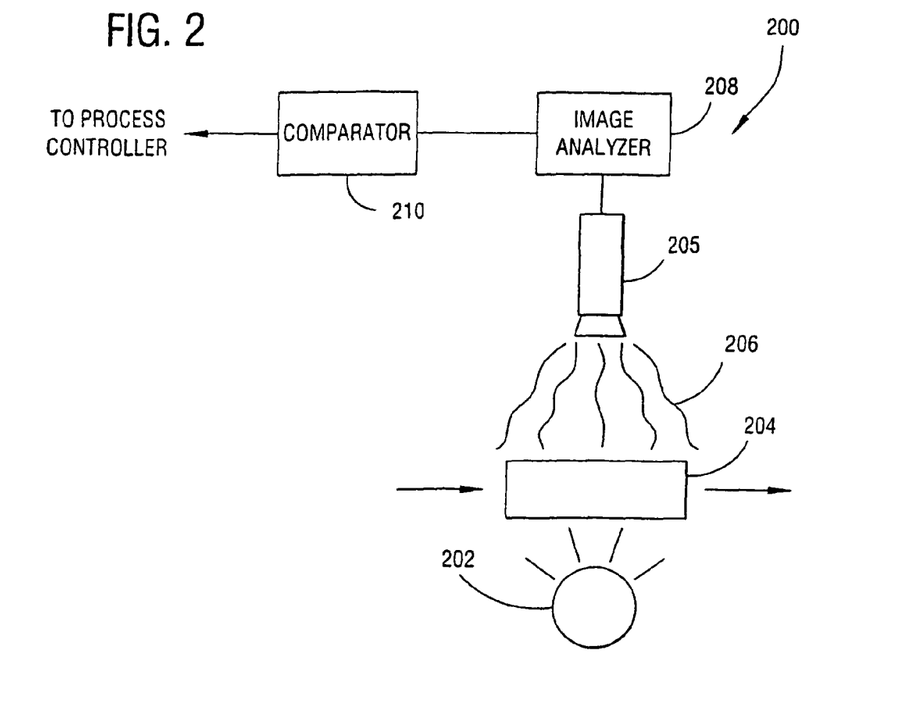
FIG. 2 is a block diagram of an exemplary system for implementing various aspects of the present invention, including the process of FIG. 1, where a composite article is positioned between an infrared detector and a radiation source.

One exemplary system 200 for implementing the process 100 of FIG. 1 (and other aspects of the present invention) is illustrated in FIG. 2. As shown therein, the system 200 includes an infrared radiation source 202 for irradiating a composite article 204 with infrared radiation. The system 200 further includes an infrared detector 205 for producing, in this example, a two dimensional image from infrared radiation 206 transmitted through the composite article 204. The infrared detector 205 is operatively connected to an image analyzer 208, which itself is operatively connected to a comparator 210.

The arrows in FIG. 2 are intended to represent constant or intermittent (e.g., periodic) movement of the composite article relative to the system 200. In one embodiment, the composite article is moved into a field of view of the infrared detector 205 for inspection. Alternatively (or additionally), the infrared detector 205 may be moved (or have components which are moved, such as in a scanning motion) for inspection of the composite article.

The infrared radiation source 202 may emit infrared radiation (i.e., radiation having a wavelength between about 700 nanometers and 1 millimeter) continuously or intermittently. If the radiation source 202 emits continuously, the detector 205 may be shuttered (electronically or otherwise) to prevent blurring of the image due to high speed movement of the composite article, if applicable. If the radiation source emits radiation intermittently, the detector is preferably synchronized with the radiation source so as to produce an image contemporaneously with the irradiating of the composite article.

The image analyzer 208 is configured to receive the image produced by the infrared detector 205. This image will include variations therein which correspond to variations in radiation levels (and/or wavelengths) received by the infrared detector from a top side of the composite article 204. In one embodiment, the image produced by the infrared detector 205 is a black-and-white image in which radiation level variations are depicted in varying grayscale levels. Alternatively, such variations may be depicted in the image in another manner, such as in the form of color variations. Regardless of their form, the image analyzer 208 is preferably configured to identifying the position of one or more variations in the produced image each corresponding to an edge position of a component in the composite article. These identified positions are then compared by the comparator 210 with reference data (e.g., ideal or predetermined position data) to determine whether the positions of components in the composite article are acceptable. For example, the comparator may determine whether the edge position of a particular component is precisely where it is supposed to be, or whether it falls within a predetermined range of acceptable positions.

The image analyzer can be configured to determine the positions of variations in the image produced by the infrared detector, and thus the edge positions of components in the composite article, either as fixed positions or relative positions, or a combination of both. Thus, the image analyzer may determine the edge position of a composite article component relative to a fixed point, edge or region of or in the image, relative to another component or the edge of another component in the image, relative to a registration mark on or about a component of the composite article, etc. As one example, the image analyzer may first determine the edge position of a first component as a fixed position (e.g., in terms of x,y coordinates or, in the case of a three dimensional image, in terms of x,y,z coordinates), and then determine the edge position of a second component (or another edge position of the first component) relative to the previously determined edge position of the first component.

The comparator is preferably configured to compare positions identified by the image analyzer with reference data (e.g., predetermined fixed and/or relative position data, as applicable) to thereby determine whether one or more components are properly positioned in the composite article. Depending on the outcome of such comparison(s), the comparator may output one or more signals to a process controller indicating that one or more composite articles should be culled and discarded, that the process should be adjusted so as to bring out-of-position components into proper position, that the process should be adjusted so that subsequent components are brought into proper registration with one another, etc. The comparator may also sound an operator alarm (such as an audible alarm) upon determining that one or more components of a composite article, or a series of composite articles, are mispositioned, and may display an image of the composite article or the components thereof to an operator for monitoring, tracking or diagnostic purposes.

Figure 3A:
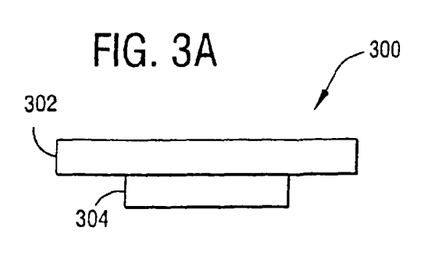
Figure 3B:
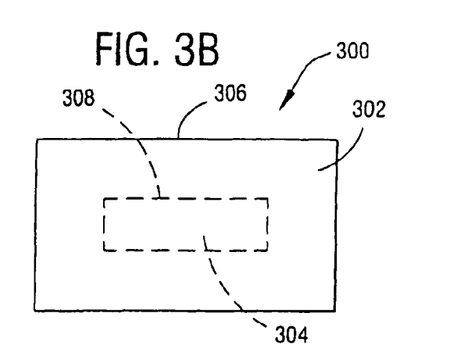
Figure 3C:
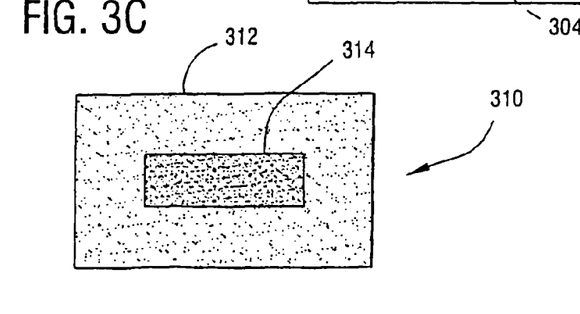

FIGS. 3(a) and 3(b) illustrate a composite article 300 which represents just one possible configuration of the composite article 200 shown in FIG. 2. As best shown in FIG. 3(a), the composite article 300 includes an upper component 302 and a lower component 304 which underlies a portion of the upper component 302. As shown in FIG. 3(b), the upper component 302 includes an edge 306, and the lower component 304 includes an edge 308. In this embodiment, both the upper component 302 and the lower component 304 partially inhibit infrared radiation from passing therethrough (e.g., by absorbing and/or reflecting some of such radiation). FIG. 3(c)

illustrates an exemplary two dimensional black-and-white image 310 of the composite article 300 as produced by the system 200 of FIG. 2. In this example, darker regions of the image 310 correspond to portions of the composite article 300 from which the infrared detector received relatively less infrared radiation. Thus, a position of one contrast variation (i.e., from light to medium) 312 in the image 310 represents a position of the upper component's edge 306. Similarly, a position of another contrast variation (i.e., from medium to dark) 314 in the image 310 represents a position of the lower component's edge 308. In fact, the entire boundary of the lower component 304 is readily apparent in the image 310 of FIG. 3(c).

The lower component 304 appears darker in the image 310 than those portions of the upper component which do not overlie the lower component since the infrared radiation which passes through the lower component 304 is partially absorbed or reflected by the upper component 302. In other words, the upper component and the lower component provide a cumulative absorptive and/or reflective effect in those regions where the upper component overlies the lower component. Therefore, the infrared detector receives less infrared radiation from that portion of the upper component which overlies the lower component than it does from surrounding portions of the upper component (assuming all portions of the upper component uniformly inhibit the same amount of infrared radiation from passing therethrough, although this is not a requirement of the invention).

By processing the image 310 of FIG. 3(c), the image analyzer 208 can identify positions of the aforementioned variations and thus provide identified position data to the comparator 210. In one embodiment, each pixel or element of the image 310 is assigned a grayscale value of 0-255, where higher grayscale values represent areas from which relatively less infrared radiation was received by the infrared detector. The image analyzer identifies predefined variations in these grayscale values which correspond to the component positions. The comparator then compares this position data with predefined position data to determine whether the upper component and the lower component are properly positioned in an absolute sense and/or with respect to one another, and output appropriate signals to the process controller.

In the embodiment described immediately above, both the upper component 302 and the lower component 304 partially inhibited infrared radiation from passing therethrough (e.g., by absorbing and/or reflecting such radiation). As should be apparent, the lower component could be similarly detected through the upper component if the lower component prevents all infrared radiation incident thereon from passing therethrough.

Infrared Blockers

In accordance with one aspect of the infrared detection system for the inspection of composite articles described herein, the degree to which one or more components of the composite article absorbs or reflects infrared radiation, and hence the degree to which the component can be detected by the infrared system, can be significantly increased by introducing one or more marking compounds, such as "infrared blockers" or "infrared markers," into the component or components of interest in a composite product. Infrared blockers have the capacity to absorb (absorbing infrared blockers) or reflect (reflecting infrared blockers) infrared light over a pre-specified wavelength range determined by a combination of the emission source output wavelength, the range of sensitivity of a detector, and the specific blocker. The infrared blockers are introduced into or onto the desired component prior to inspection of the composite product with the infrared detection system described herein, and can be applied to the component(s) in the form of dyes, films, tags, paints, other coatings, etc., as further discussed herein. The introduction of such infrared blockers can significantly increase the absorbence or reflectance of the component of interest in the composite product resulting in an improved image which can more precisely detect and pinpoint the cross direction and/or machine direction position of one or more components of the composite article.

1. Absorbing Infrared Blockers

When absorbing infrared blockers are utilized in one or more components of the composite article being inspected, a back lighting geometry is typically utilized wherein the light emitted from any number of infrared sources is significantly absorbed at either specific or broad wavelength regions so that it cannot reach the detector which is located on the opposite side of the source. A suitable geometry setup for using absorbing infrared blockers is shown in FIG. 2. Although less preferred, other lighting geometries known to those skilled in the art can be utilized in accordance with the present invention in combination with absorbing infrared blockers.

Absorbing infrared blockers suitable for use in the present invention include high absorption coefficient infrared absorbing dyes, highly absorbing materials such as filters and dielectrics capable of selectively absorbing light, or dark materials which absorb a broad band of light.

A list of filter types which could be used to block specific wavelengths of light include dielectric interference filters made from films, neutral density filters, colored films, high-pass and low-pass films, edge reflective films, and other films containing dyes or light-blocking materials. For dielectric filter interference, filters are designed to transmit light for only a defined spectral bandpass, conversely they are used for blocking light over adjacent bands. These filters are comprised of a solid Fabry-Perot cavity. Interference films can be made by a sandwich of two partially reflective metallic film layers and are separated by a transparent dielectric spacer film layer. The partially reflective layers are made of higher refractive index than the dielectric spacer layer and have a thickness close to one-fourth the desired transmittance peak wavelength. The lower refractive index spacer layer is made to a thickness of one-half the desired transmittance peak wavelength. The thickness of the dielectric spacer layer determines the actual peak transmission wavelength for the filter. The actual wavelength position of the transmittance peak through a Fabry-Perot, interferometer based, interference filter is given as:

$$\lambda_M = 2 \times n_s t_s \cos \theta / i$$

where $\lambda_M$ is the wavelength of maximum transmittance for the interference filter composite (in micrometers), $n_s$ is the refractive index of the dielectric spacer, $t_s$ is the thickness of the dielectric spacer in micrometers, $\theta$ is the angle of incidence of the light impinging onto the dielectric spacer, and i is the nonzero integer order-number for the interference as (1, 2, 3, 4, . . . n). The wavelength of peak transmittance for an interference filter can be moved by varying the angle of incidence ($\theta$) of collimated light onto the surface of the filter. The relationship defining the peak position of maximum transmission is given as:

$$\lambda_{M'} = \lambda_M \{1 - (n_A/n_S)^{1/2} \sin^2 \theta$$

where $\lambda_{M'}$ is the wavelength of the new peak transmission position at an incidence angle greater than 0 degrees, $\lambda_M$ is the wavelength of maximum transmittance for the interference filter composite (in micrometers) from the previous equation, $n_A$ is the refractive index of the surrounding medium (air=1.0003), $n_S$ is the refractive index of the dielectric spacer, and θ is the angle of incidence of the light impinging onto the dielectric spacer. The technology for making these filters is well-known and has been described in multiple references for glass substrates. The conventional materials are commercially available as per specifications from such suppliers as Melles Griot and Edmund Scientific. Films are described in U.S. Pat. No. 3,711,176, U.S. Pat. No. 5,103,337, and WO 96/19346, and WO 97/17303. Similar films are commercially available through Edmund Scientific and other commercial optical suppliers. For this present invention the material structure to be registered is laminated with the dielectric-based film acting as an interference filter. The wavelength selected for measurement illumination must be attenuated by the bulk of the manufactured structure while the structure to be registered transmits more light and thus is lighter colored to provide the registration profile.

Dark materials suitable for use in the present invention are those materials with an optical density difference of at least 1.0 as compared to the surrounding media. The optical density ($O.D._T$) value for transmittance is given as:

$$O.D._T = \log_{10}(100/T_P)$$

where $O.D._T$ is the optical density of a material at a specific wavelength, and $T_P$ is the percent transmittance of the material at a specific wavelength.

Particularly preferred absorbing infrared blockers for use in the present invention are high absorption coefficient infrared absorbing dyes. Generally speaking, absorbing infrared blockers are selected for use in the present invention based on their safety, cost efficiency and high extinction coefficient (i.e., absorptivity) for their intended use. Preferred dyes are typically selected based on a combination of factors including: (1) safety issues relative to exposure limits; (2) high absorptivity; (3) solubility; (4) center wavelength of maximum blocking or optical absorbence; and (5) full width at half-maximum bandwidth. The most useful dyes preferably do not contain antimony, nickel, or other heavy metals represented on the periodic table as Period 4, Groups IIIA through VIB, and Period 5, Groups IA through VIB due to safety and disposal issues. Preferred dyes contain a majority of the elements carbon, hydrogen, and oxygen, with nitrogen, sodium, and chlorine typically permitted in low molar concentrations, preferably less than 10 percent mole fraction for each element.

Suitable absorbing infrared blockers for use in the present invention desirably have an absorption peak maximum within the range of from about 750 nm to about 1200 nm, more desirably from about 750 nm to about 1150 nm, and still more desirably from about 775 nm to about 1050 nm. Further, the absorbing infrared blockers desirably have an extinction coefficient within the range of from about $1 \times 10^4$ L/mole cm to about $5 \times 10^5$ L/mole cm or more, and more desirably from about $5 \times 10^4$ L/mole cm to about $3 \times 10^5$ L/mole cm or more, and most desirably, the extinction coefficient will be about $1.5 \times 10^5$ L/mole cm or more. In this regard it is to be noted that essentially no upper limit to the extinction coefficient applies, and that safe materials having higher absorptivities are preferred, as materials with higher absorptivities increase the contrast in the resulting visual image, allowing for increased detection.

Various types of absorbing infrared dyes are suitable for use in the present invention including, for example, solvent soluble absorbing infrared dyes, water soluble absorbing infrared dyes, and metal complex absorbing infrared dyes. Solvent soluble absorbing infrared dyes are typically soluble in chloroform and petroleum ether, as well as other non-polar organic solvents. Water soluble absorbing infrared dyes are soluble in water, as well as alcohols and glycols. Suitable solvent soluble and water soluble absorbing infrared blockers for use with the composite components described herein can have the empirical formulas shown in (I) and (II), respectively:

$$C_xH_yN_z(R^1)_w(R^2)_v \quad (I)$$

$$C_xH_yN_z(R^1)_w(R^2)_v(R^3) \quad (II)$$

wherein x is a whole number from 30 to 70, preferably from 32 to 62, y is a whole number from 32 to 112, preferably from 36 to 96, z is a whole number from 0 to 6, $R^1$ is selected from the group consisting of Cl, O, and Sb, wherein w and v are whole numbers from 1 to 12, $R^2$ is I or O when $R^1$ is Cl, S when $R^1$ is O, and F when $R^1$ is Sb, and $R^3$ is selected from the group consisting of F and S. Some water soluble forms of the blocking compounds described herein may be in the form of a salt having, for example, a sodium or potassium cation.

Examples of solvent soluble absorbing infrared dyes commercially available from American Dye Source, Inc., and suitable for use in the present invention include, but are not limited to those shown in Table 1:

TABLE 1

| Catalog No. | Wavelength (nm) | Chemical Formula |
|---|---|---|
| ADS775MI | 775 | $C_{32}H_{36}ClN_2I$ |
| ADS775MP | 775 | $C_{32}H_{36}ClN_2O_4$ |
| ADS775HI | 780 | $C_{44}H_{60}ClN_2I$ |
| ADS775PI | 780 | $C_{36}H_{44}ClN_2I$ |
| ADS775PP | 780 | $C_{36}H_{44}Cl_2N_2O_4$ |
| ADS780MP | 780 | $C_{31}H_{34}Cl_2N_2O_4$ |
| ADS780HO | 780 | $C_{34}H_{40}N_2O_6C_{12}$ |
| ADS800AT | 798 | $C_{54}H_{54}N_2O_4S$ |
| ADS805PI | 805 | $C_{35}H_{42}ClN_2I$ |
| ADS805PP | 803 | $C_{35}H_{42}Cl_2N_2O_4$ |
| ADS805PA | 803 | $C_{31}H_{34}Cl_2N_2O_4$ |
| ADS805PF | 803 | $C_{37}H_{42}F_3ClN_2O_2$ |
| ADS812MI | 812 | $C_{40}H_{40}ClN_2I$ |
| ADS815EI | 815 | $C_{42}H_{44}ClN_2I$ |
| ADS818HI | 818 | $C_{52}H_{64}ClN_2I$ |
| ADS818HT | 818 | $C_{59}H_{71}Cl_2N_2SO_3$ |
| ADS822MT | 822 | $C_{53}H_{52}N_2O_3S_2$ |
| ADS830AT | 813 | $C_{47}H_{47}ClN_2O_3S$ |
| ADS838MT | 838 | $C_{46}H_{45}ClN_2O_3S$ |
| ADS840MT | 841 | $C_{37}H_{35}ClN_2O_3S$ |
| ADS845BI | 845 | $C_{36}H_{40}ClN_2I$ |
| ADS905AM | 905 | $C_{62}H_{96}N_6SbF_6$ |
| ADS956B1 | 956 | $C_{36}H_{40}Cl_2N_2O_4$ |
| ADS104OP | 1046 | $C_{55}H_{54}ClO_6$ |
| ADS1045P | 1048 | $C_{47}H_{39}ClO_6$ |
| ADS1050P | 1048 | $C_{49}H_{42}ClO_6$ |
| ADS1060A | 1060 | $C_{62}H_{92}N_6Sb_2F_{12}$ |
| ADS1065A | 1060 | $C_{62}H_{92}N_6Sb_2F_{12}$ |
| ADS1120P | 1120 | $C_{52}H_{44}Cl_2O_6$ |

Examples of water soluble absorbing infrared dyes commercially available from American Dye Source, Inc., and suitable for use in the present invention include, but are not limited to, those shown in Table 2:

TABLE 2

| Catalog No. | Absorption | Chemical Formula |
|---|---|---|
| ADS780WS | 781 | $C_{38}H_{46}ClN_2O_6S_2Na$ |
| ADS785WS | 785 | $C_{43}H_{47}N_2O_6S_2Na$ |
| ADS790WS | 791 | $C_{44}H_{52}N_3O_6S_3Na$ |
| ADS805WS | 807 | $C_{36}H_{44}ClN_2O_6S_2Na$ |
| ADS820WS | 820 | $C_{42}H_{49}N_2O_6S_3Na$ |
| ADS830WS | 822 | $C_{46}H_{51}ClN_2O_6S_2Na$ |
| ADS850WS | 844 | $C_{45}H_{48}ClN_2O_6S_2Na$ |

Additionally, metal-based metal complex absorbing infrared dyes can be utilized in accordance with the present invention. Suitable metal complex absorbing infrared blockers for use in the present invention commercially available from American Dye Source, Inc. include, but are not limited to, those shown in Table 3:

TABLE 3

| Catalog No. | Absorption (nm) | Chemical Formula |
|---|---|---|
| ADS845MC | 845 | $C_{28}H_{40}Cl_4NS_4Ni$ |
| ADS870MC | 867 | $C_{28}H_{38}Cl_6NS_4Ni$ |
| ADS880MC | 882 | $C_{32}H_{28}S_4Ni$ |
| ADS885MC | 885 | $C_{32}H_{26}O_4S_4Cl_2Ni$ |
| ADS890MC | 892 | $C_{30}H_{48}NS_4Ni$ |
| ADS920MC | 922 | $C_{32}H_{28}O_4S_4Ni$ |
| ADS990MC | 990 | $C_{32}H_{30}N_2N_4Ni$ |

Suitable absorbing infrared dyes for use in the present invention typically have molecular weights ranging from about 450 g/mol to about 1450 g/mol, and desirably from about 600 g/mol to about 825 g/mol. The molecular weight of the dye may be an important consideration relative to its dispersibility and solubility for adding to the polymer films. The colors of absorbing infrared blockers range from light gray to dark green, the lighter colors having high absorptivity values being more desirable.

Generally, the absorbing infrared blockers are added to the desired component of the composite article in an amount sufficient to increase the detectability of the desired component in the infrared inspection system described herein relative to other components in the composite article. Typically, the absorbing infrared blockers can be added to materials for registration by introducing the blocking compounds into the particular component at a concentration of at least about 10 parts per billion and more desirably at a concentration of at least about 10 parts per million. In certain circumstances where the desired absorbing infrared blocker has a relatively low absorptivity, the blocker can be added at a level of up to about 10% (weight/weight). In most cases, a concentration of absorbing infrared blocker from about 10 parts per million up to about 1% or 2% (weight/weight) is sufficient to impart the desired benefits on the treated component.

In accordance with the present invention, there are several methods that can be utilized to introduce the absorbing infrared blocker, such as an absorbing infrared dye, into or onto a component of a composite product to improve the detectability of the component as compared to other untreated components of the article. It will be recognized by one skilled in the art that one or more absorbing infrared blockers can be introduced into one or more components of the composite article.

In one method, the absorbing infrared blockers described herein for use in the present invention can be introduced into the desired component of the composite material by pre-mixing the blocker directly into a polymer for molding or extrusion into various plastic structures or films for use in a composite article. In this embodiment, the blocker is added directly into the polymer and the mixture is agitated to blend the blocker prior to the polymer/blocker mixture being molded or extruded into a structure or film. Once the polymer/blocker mixture is molded or extruded into a desired component, the blocker is contained within the component and can improve detectability of the component as described herein through increased absorption of infrared radiation.

In an alternative embodiment, the absorbing infrared blockers can first be mixed with a solvent and dissolved therein, and then the solution introduced into a polymer for molding or extrusion. In this embodiment, the solvent/absorbent blocker solution is typically continuously agitated throughout the molding or extrusion process to ensure that the solution is homogeneous and the amount of settling out of the blocker, if any, during molding is minimized. During molding or extruding, the solvent part of the solution is typically evaporated off, resulting in a component containing the desired blocker. In a related embodiment, the blocker can be batch-mixed with an adhesive or ointment which is ultimately introduced onto a component of the composite product. This embodiment allows for registration of the adhesive or ointment relative to one or more other components.

Regardless of whether the absorbing infrared blocker is added directly to the polymer, or added to the polymer as a solution containing a solvent, the blockers are preferably stable at extrusion temperatures of from about 70° C. to about 300° C. Additionally, the blockers are preferably efficacious and substantially chemically stable throughout the time of manufacture up to and including 15 days beyond the storage and manufacturing use time.

In a further alternative embodiment, the absorbing infrared blockers can be made into a paint or coating compound and introduced onto any surface layer of a single or composite polymer film or structure. In this embodiment, the blocker is typically mixed with a carrier compound and introduced or painted directly onto a component and allowed to dry prior to the component being inspected as described herein. Similarly, the blockers described herein can be blended into a printable ink for use in printing specific patterns onto polymer films and structures.

In a further alternative embodiment, the absorbing infrared blockers can be combined with a carrier resin such as a linear low density polyethylene or polypropylene and the mixture heated and melted to create a solution comprising the absorbing infrared blocker. This solution or hot melt can then be applied directly onto the desired component of the composite article to introduce the blocker onto the component. The amount of blocker and carrier resin used to create the hot melt can vary depending upon the desired concentration of blocker resulting on the component.

Alternatively, the infrared blockers can be printed directly into or onto a component of a composite product, or can be applied in a liquid or powder form from a feeder or sprayer. One skilled in the art will recognize that there are other methods that could be utilized to introduce the infrared blockers described herein into or onto one or more components of a composite article to achieve the intended benefits. As such, the examples of various methods included herein should be taken as illustrative and not as limiting in any manner.

Regardless of the manner in which the absorbing infrared blockers are introduced into or onto the component of the composite article, the blocker is preferably substantially chemically non-reactive with the polymers, polymer additives, adhesives, and polymer coatings. Further, it is preferable that the blockers not bleed out or migrate from the components in which they are introduced, as this may result in a less detectable component.

A. Reflecting Infrared Blockers

Figure 4:
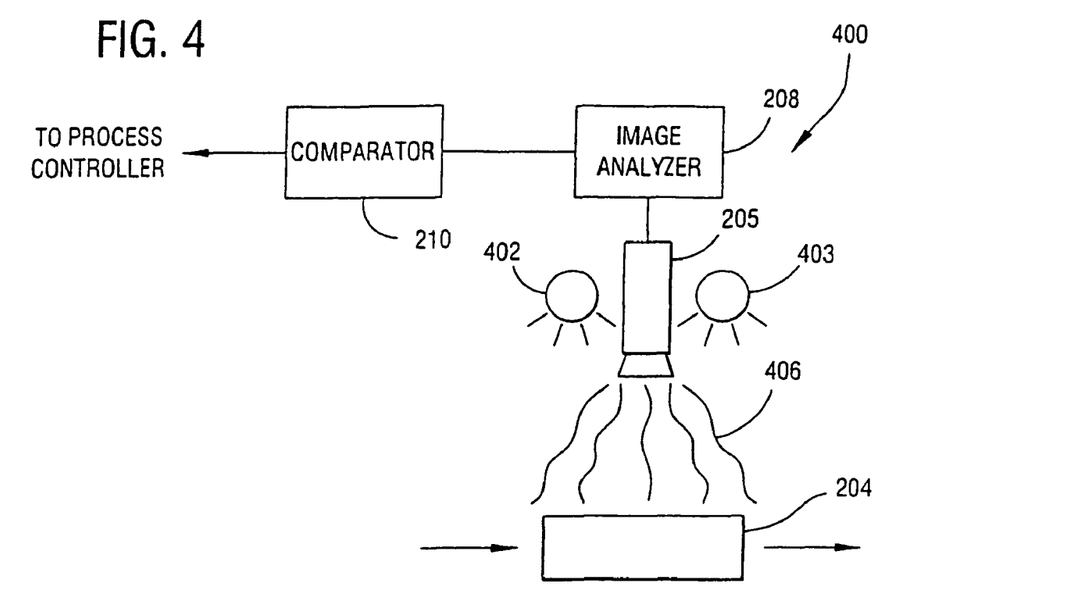
FIG. 4 is a block diagram of another exemplary system for implementing various aspects of the present invention, including the process of FIG. 1, where the infrared detector and radiation sources are positioned on the same side of the composite article.

Alternatively, reflecting infrared blockers can be utilized in accordance with the present invention to improve the detectability of one or more components of a composite article. When reflecting infrared blockers are utilized in one or more components of the composition being inspected, a gloss image can be used for registration by detecting the reflected image from the surface of the viewed object. This optical geometry is accomplished by positioning the infrared source and the detector on the same side of the viewed object. The angle of illumination and detection between the source and the detector relative to the viewed object is from about zero degrees to about 90 degrees, and preferably is about 45 degrees to allow for maximum detectability. The incident light is reflected from the reflecting blocker surface and detected at preferably a 45 degree angle as this angle reduces the glossy surface reflection of the object relative to the reflection of the infrared blocker. A suitable setup for using reflecting infrared blockers is shown in FIG. 4.

In one embodiment utilizing reflecting infrared blockers, infrared light can be reflected off of one or more components of a composite article during registration utilizing multilayer reflective films which provide light reflectance characteristics over a broad and pre-specified range of wavelengths, as discussed below. By varying the optical thickness of a sandwich of two or more layers of optically active films, a multilayer reflective film can be designed that reflects light over a broad band of wavelengths. This band is often referred to as the reflection band, or stop band. Such multilayer reflective films comprising alternating layers of two or more polymers to reflect light are described in, for example: Wheatley et al. (PCT Application Nos. WO 99/36809 and 99/36810); Alfrey, Jr. et al. (U.S. Pat. No. 3,711,176); Schrenk et al. (U.S. Pat. No. 5,103,337); Jonza et al. (PCT Application No. WO 96/19347); and, Ouderkirk et al. (PCT Application No. WO 95/17303); all of which are incorporated herein by reference.

The reflection and transmission spectra of a particular multilayer film depend primarily on the optical thickness of the individual layers. Optical thickness may be defined as the product of the actual thickness of a layer times its refractive index. By using this relationship, suitable multilayer films can be designed to reflect infrared light, as well as visible and ultraviolet light, by choosing the appropriate optical thickness of the layers in accordance with the previously referenced art, as described using Equation (A):

$$\text{Wavelength}_f = (2/I)^* T_R \tag{A}$$

wherein I is an integer representing the particular order of the reflected light (as 0, 1, 2, etc.), and $T_R$ is the thickness of an optical repeating unit (also called a multilayer stack), consisting of two or more polymer layers, $T_R$ is always one-half wavelength in thickness, where wavelength is the first order reflection peak. By varying the optical thickness of an optical repeating unit within a multilayer film structure, a multilayer film can be designed to reflect light over a specific wavelength region such that the resulting multilayer reflective film can be used in a composite article for registration.

Wavelength regions are typically shortwave near infrared or from approximately 690 to 1200 nanometers (0.69 to 1.2 microns), preferably 750 to 1100 nanometers (0.75 to 1.1 microns). Wavelength regions above and below this region could also be utilized in a less preferred embodiment; especially 0.69 microns to 2.5 microns. Although this less preferred region can be utilized in accordance with the present invention, it is typically less preferred as detection systems for this region are typically expensive.

Although utilizing multilayered films is within the scope of the present invention, it is typically less preferred than blocking dyes or scattering approaches discussed herein due to the complexity and cost of the multilayered film construction. Suitable materials are commercially available, but cost considerations for mass production must be considered prior to use. Most commercially available materials are constructed specifically for desired center wavelength of light transmission, bandwidth of light transmitted, and cost. The thickness and number of layers for the construction of these films is determined by these performance specifications. Typically, multilayered interference films are made using a glass or quartz substrate. However, polymer film-based filters could be laminated into the registration structures using adhesives or other forms or bonding such as precision thermal annealing or ultrasonic bonding.

Figure 8:
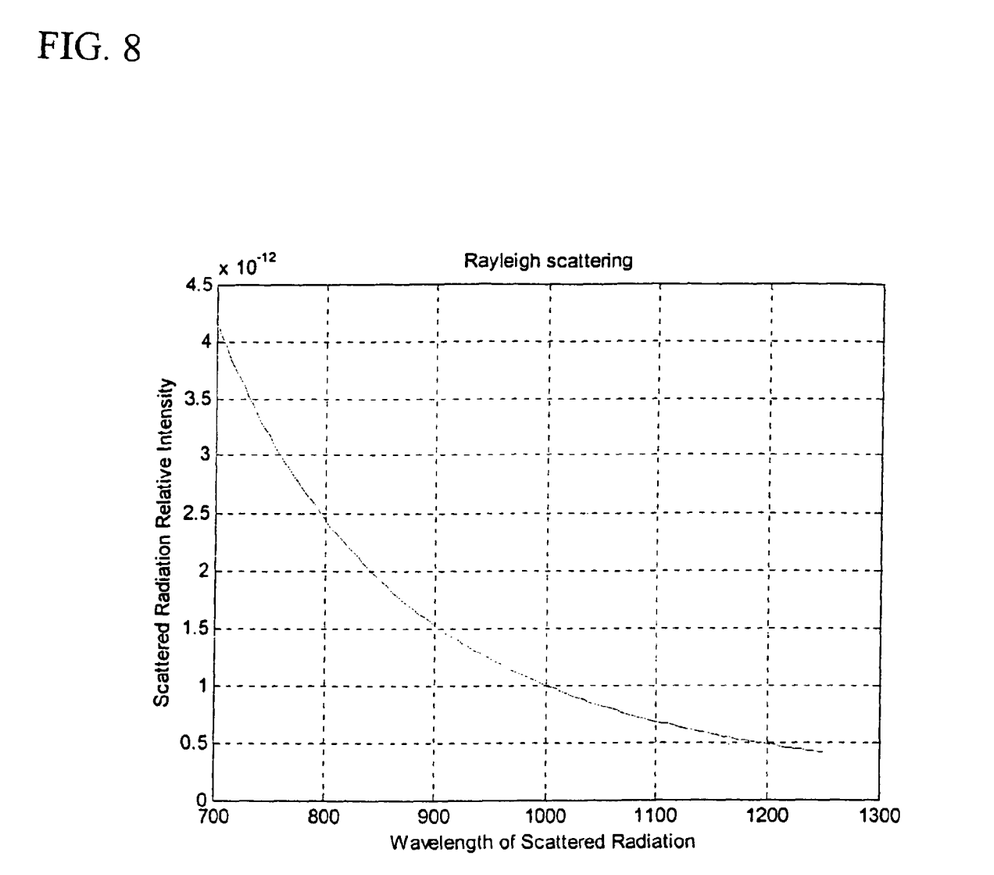
FIG. 8 illustrates Equation B (as further described herein), showing relative light scattering under identical conditions as a function of wavelength.

In an alternative embodiment, particle light scattering compounds can be utilized to create the desired infrared radiation reflectance to improve component detectability. In particle light scattering, such as what is referred to as Rayleigh scattered light, the intensity of the scattered energy ($I_{RS}$) is inversely proportional to the 4th power of the incident light energy ($\lambda$), as given by Equation (B) and illustrated in FIG. 8.

$$I_{RS} \propto 1/\lambda^4 \tag{B}$$

Typically, the optimum wavelengths of light for utilizing the particle light scattering phenomenon are those below about 1150 nanometers, preferably below about 950 nanometers, and preferably from about 750 to about 850 nanometers. However, the longer near infrared wavelengths above 950 nm are also useable, even though they demonstrate lower relative intensity, and are therefor less preferred.

A scattering reflection technology can be based upon the optical physics modeled by the relationship:

$$I_s/I_o = 1/r^2 * (2\Pi/\lambda)^{4*} \alpha^2 \sin^2 \theta \tag{C1}$$

wherein
 $I_s$ is the scattered or reflected light;
 $I_o$ is the total incident light intensity;
 r is the average particle radius;
 $\lambda$ is the wavelength of the incident radiation;
 $\theta$ is the reflected light angle, assuming the incident energy is normal to the viewed surface of an object; and,
 $\alpha$ is a proportionality factor, given as $\alpha = n^2 - \frac{1}{4}\Pi d$, where n is the refractive index of the particles scattering or reflecting light and d is the particle density in numbers of particles per cubic cm ($cm^{-3}$).

Highly reflective particles, typically defined as particles with an extremely low reflection extinction coefficient (i.e., high reflectivity) for the wavelength region of interest, such as a wavelength of less than about 950 nanometers, preferably less than about 850 nanometers, and more preferably less than about 750 nanometers, can be utilized to create the desired light scattering effect to improve detection. These highly reflective particles are composed of a mean particle size and density such that the ratio of the scattered or reflected light, as compared to the incident illumination ($I_s/I_o$) described in the preceding mathematical relationship is maximized to about 0.15 (15%) or greater, preferably about 0.5 (50%) or greater, and most preferably about 0.90 (90%) or greater. It should be noted, however that the maximum value obtainable is near about 1 (100%), and that values within the range of about 0.90 (90%) to 1.0 (100%) are most preferred in accordance with the present invention.

The size for light scattering particles roughly spherical in shape are to have a mean diameter of less than 2 times the wavelength of the incident energy used for registration detection. The maximum particle size should have a diameter of less than 2.5 times the wavelength of the incident energy used for registration detection. It is preferred that the mean particle diameter be from 0.5 to about 1.5 times the wavelength of the incident energy used for registration detection. The particle size distribution is preferably such that 95 percent of the particles have diameters within 0.25 to 2.5 times the wavelength of the incident energy used for registration detection. Particles exceeding 3 times the incident wavelength will have little value for reflecting light either as a reflection device or as a blocking device.

Figure 9:
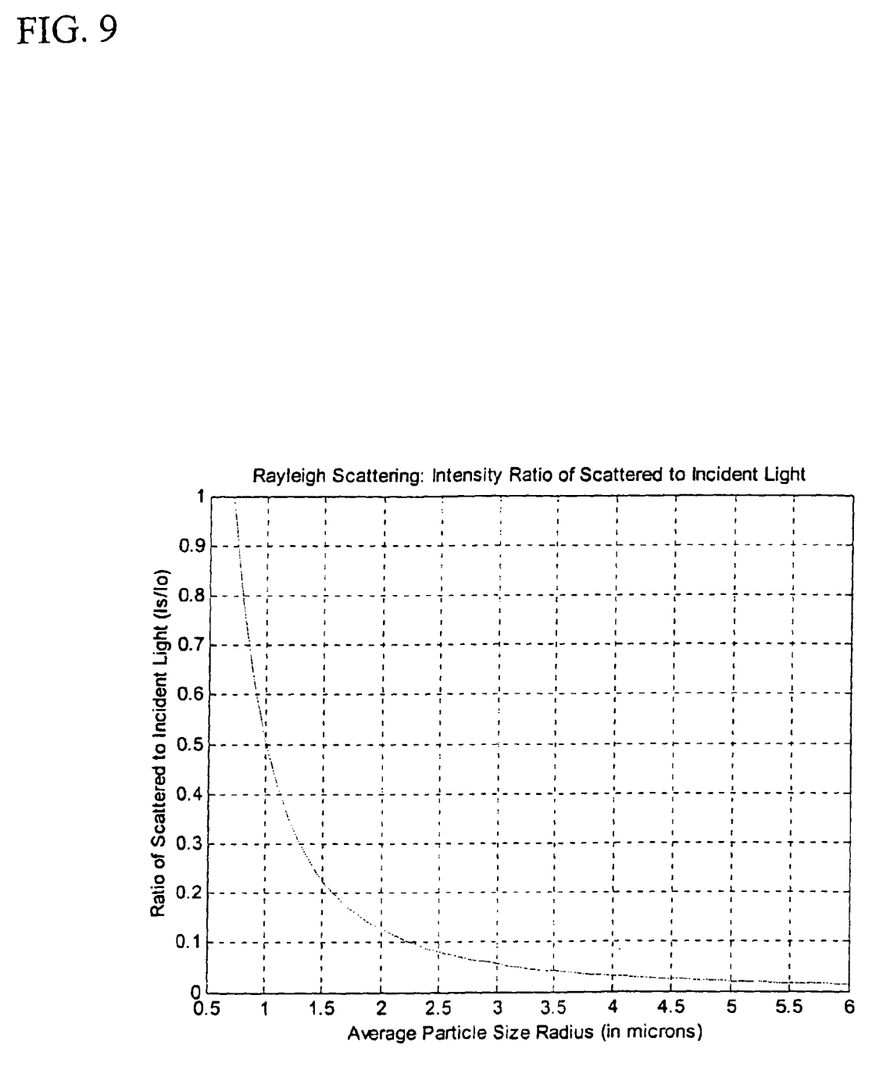
FIG. 9 illustrates Equations C1 and C2, showing the ratio of scattered to incident light ($I_s/I_o$) as a function of the average light scattering particle radius (in microns) for a nominal set of conditions.

Accordingly, safe materials with higher ratios of the scattered or reflected light, as comparted to the incident illumination ($I_s/I_o$), are more favorable should they become available. This property can be measured directly, using a standard spectrophotometer covering the wavelength region of interest. The determination is made by measuring the reflectance of a reflectance reference standard with predetermined reflectance values near about 100%, correcting the reflectance spectrum to those values and measuring the test material. When using a ratioing spectrophotometer, the resultant reflectance or percent reflectance can be displayed. The reflectance value is equivalent to the intensity ratio of scattering to incident light ($I_s/I_o$) for the measurement conditions used. FIG. 9 illustrates the case for a 1 micron wavelength illumination in air, a 1 degree from normal angle of observation, particles with a refractive index of about 2.5, and a constant density of particles per unit volume. Accordingly, the use of Equations C1 and C2 provide a computation of the dependency of the mean particle size to the intensity ratio of scattered to incident light.

The scattering particles consisting of compounds described herein are composed of the appropriate calculated mean particle size. These particles can be extruded into polymer structures and films at low temperatures (typically less than about 250° C.), or they can be added to adhesives, printable latexes and print bases, or as ingredients to standard paint bases for application to the desired component of the composite article. When reflective materials are added to films, they are preferably selected to be stable at extrusion temperatures (e.g., from about 70° C. to about 300° C.), and are efficacious and chemically stable throughout the time of manufacture (up to and including about 15 days beyond the storage and manufacturing use time). Greater stability is desirable but not required.

The reflective components are preferably substantially chemically non-reactive with polymers and polymer additives (such as polyolefin films and webs, or cellulose), or with adhesives or polymer coatings. The reflective components also are preferably selected so as not to bleed out of the structure over the manufacturing use period. The safety of such components typically applies to human use in the relative concentrations required for efficient reflection enablement.

Particle density in the reflective substrate is preferably such that the light reflection for the optically reflective material is at least one order of magnitude more highly reflective as compared to the surrounding material; this is represented by at least 1.0 optical density unit where optical density ($O.D._R$) value for reflection is given as:

$$O.D._R = \log_{10}(100/R_P)$$

where $O.D._R$ is the optical density of a material at a specific wavelength, and $R_P$ is the percent reflectance of the material at a specific wavelength. The concentration of particles is evaluated for different levels to empirically determine the optimum coverage to meet these reflectance criteria.

In view of the foregoing, the precise concentrations of scattering particles required is typically determined by making a serial dilution of scattering particles into the film and determining the optimum scattering as $I_s/I_o$, which provides a precise estimate of particle size and concentration useful for appropriate reflection levels. When these measurements are combined with Equation D, below, an appropriate contrast can be determined for any specific application. The concentration of scattering particles in or on a film structure typically ranges from about 0.1% to about 20% by weight, preferably from about 0.5% to about 5%, and more preferably is less than about 2% by weight (e.g., from about 1% to less than about 2%).

The present invention provides for the use of scattering particles within a composite product for positioning of product components during the manufacture assembly. Suitable materials which can be used to add reflection properties to these registration structures include, for example, low cost films containing titanium dioxide ($TiO_2$), barium sulfate ($BaSO_4$), magnesium oxide (MgO), calcium carbonate ($CaCO_3$), porous and non-porous polytetrafluoroethylene (e.g., Teflon®) micron beads, or polyolefins micro beads (such as polypropylene or polyethylene) of appropriate size for light scattering.

Accordingly, using Equations C1 and C2, a preferred particle size can be calculated (see FIG. 9 for a nominal set of registration conditions). The refractive index of the materials comprising the particles is preferably greater than about 1.5, more preferably greater than about 2, and most preferably greater than about 2.5. The high refractive index inorganic materials are not water soluble, but are dispersible, and are preferably added to film structures by extrusion into structures and films at low temperatures (e.g., less than about 250° C.). Inorganic materials and polymer micro beads, such as those conventionally used for affinity chromatography, with a mean particle size or radius of about 1 micron can be added to adhesives, printable latexes and print bases, or as ingredients to paint. The micro beads are suspended in a fixable medium and can be sprayed or dipped onto the registration structures, then air dried to produce the desired light scattering effect.

For reflective light, the focus of the beam at the detector can be used to assess z-directional positioning of a reflecting film layer or layers. A single collimated light beam, or laser, is focused at a nominal position provided a known beam diameter of the detector. Moving the reflecting film position toward or away from the detector alters the size of the beam at the detector. Moving the reflector toward the detector reduces the beam diameter, while moving the reflector away from the detector enlarges the beam. This principle can be used to measure a relative z-axis position of a reflective surface. If two or more reflective surfaces are used, the difference in beam dimensions can be used to indicate the relative z-position between the two reflective surfaces.

Contrast is an important characteristic of registration and detection of treated structures, and therefore is to be considered in selecting an ideal reflective, absorptive, or transmissive material. Contrast is defined as the ratio of the difference between the maximum illuminance (as $I_{max}$ in units of lux) and the minimum illuminance (as $I_{min}$) of a surface exhibiting two or more distinct levels of brightness (or darkness) and the sum of the maximum and minimum illuminance. The illuminance is determined using either back-lit or front-lit detection geometry, dependent upon the use of an absorber or reflector application. If a power meter is unavailable, the values for $I_s/I_o$ may be substituted for I in Equation D. Contrast is often specified for a typical interference-diffraction pattern, given the alternating light and dark rings created by interference at a narrow slit. Contrast is described by:

$$\text{Contrast} = I_{max} - I_{min}/I_{max} + I_{min} \quad (D).$$

Maximum contrast aids in optimizing registration (a contrast of about 1 being large and about 0 being small); contrasts greater than about 0.2 thus being preferred, with contrasts of greater than about 0.5 and 0.6 being more preferred. This aspect of material and blocker selection is utilized in order to gain maximum contrast at a cost that is compatible with the specific manufacturing application. There are other characteristics which are also important in assessing the optical quality of absorbers and reflectors, including clear definition of the concept of illumination. Illumination is defined as the energy of light (E) striking a surface for a specific unit area per unit time. This definition is shown using the expression in Equation F:

$$E = (I_s \cos \alpha)/d^2 \qquad (F)$$

wherein

E is the illumination (or light energy) in lumens per mm$^2$;

$I_s$ is the source intensity in candlepower;

$\alpha$ is the angle between the source light rays and a unit vector normal to the illuminated surface; and, d is the distance, in mm, from the source to the illuminated surface.

The illumination and angle of incidence and detection can change the contrast ratios dramatically for use in registration. Thus, the optimum materials for absorbing or reflection include those exhibiting the maximum contrast at a pre-specified set of measurement conditions, including wavelength of the source, sensitivity of the detector, angle of incidence and detection, illumination geometry, source intensity and distance, and cost of absorbing or reflecting agents. These parameters are established by the cost and space requirements, as well as the restrictions of ambient lighting conditions.

The optimum set of materials, as well as illumination and detection conditions, are established by calculating the optimum absorbing and reflection values for the materials, and then measuring contrast under the anticipated measuring conditions. The use of this invention therefore provides for optimal optical contrast at a practical low cost of implementation when compared to multilayered films and other optical film technologies.

The absorbing and reflecting infrared blockers described herein for incorporation into one or more components of a composite product can be introduced into a variety of components to improve detectability of the component as compared to untreated components during infrared inspection. For example, blockers could be introduced into numerous components including side panels, adhesives, surge materials, elastic strands, superabsorbent polymer materials, waist elastic material, hook or loop or similar mechanical fastening devices, ink for graphics, attachment tapes, nonwoven sheets as utilized for outer covers or liners, and skin care ointments such as lotions or vitamin E. One skilled in the art will recognize that there are numerous other components of composite articles that could be used in combination with the blockers described herein in accordance with the infrared detection system. As such, the above listing is simply meant to be illustrative and not limiting.

As noted above and discussed herein, the infrared absorbing dyes and compounds and reflecting materials described herein can be extruded into polymer structures and films at low temperatures, typically less than about 250° C. Alternatively, they can be added to adhesives, printable latexes and print bases, or as ingredients to paints. When added to films, they are preferably stable at extrusion temperatures from about 70° C. to about 300° C., and must be efficacious and chemically stable throughout the time of manufacture, typically up to and including about 15 days beyond the storage and manufacturing use time. Additionally, the blocking compounds are generally selected to ensure: (i) they do not react with the polymer, polymer additives, adhesives or polymer coatings with which they are to be combined or mixed; and, (ii) they do not bleed out of the structures, or migrate across the surface of the structures, to be registered during the manufacturing use period. Finally, the safety of such compounds generally applies to human use in the relative concentrations required for efficient optical blocking, based on the extinction coefficient of the blocker.

Register Inspection Using IR Blockers

Once the infrared blocker is introduced into or onto the desired component of the composite article, the component can be inspected as described herein for its position relative to other components of the composite article. Specifically, infrared blockers can be introduced into spunbond laminate side panels to determine the cross direction and machine direction position of the side panels relative to the absorbent pad of the composite article. In another embodiment, infrared blockers could be introduced into the ink used to create various graphics to determine the position of the graphics relative to the absorbent pad. In a still further embodiment, infrared blockers could be introduced into a surge layer to determine the surge layer position relative to the absorbent pad. In a still further embodiment, infrared blockers could be introduced into leg elastic strands to determine the position of the leg elastic strands relative to the outer cover. In another embodiment, infrared blockers could be introduced into waist elastic to determine the position of the waist elastic relative to the absorbent pad edge. In a still further embodiment, infrared blockers could be introduced into a hook and loop type fastener to determine their position relative to the spun bond laminate edge prior to fastening; stated another way, the inspection of the placement of the hook and loop could be done while the product was still in web form.

In one embodiment of the present invention, instead of simply introducing the infrared blocker into only a single component of a composite product for registration of the single blocked component, one or more of the same or different infrared blockers can be introduced into more than one component for registration. In this embodiment, the identical infrared blocking compound can be introduced into or onto more than one component of a composite product to allow registration for numerous components and the determination of the position of each blocked component relative to other unblocked components of the composite product. Alternatively, infrared blocking compounds having different absorption characteristics could be utilized in different components of the same composite product to produce differential contrast registrations for the blocked components of the composite product. This embodiment would still allow the position of blocked components of the composite product to be determined relative to unblocked components, and would further allow differentiation of blocked components relative to each other.

In another embodiment of the present invention, the infrared blockers described herein can be utilized on one or more components of a composite article for quantitative analysis of the blocked component in the composite product. For example, a superabsorbent polymer material, which is typically introduced into the absorbent core of a composite article to imbibe liquid in this region, could be treated, prior to incorporation into the absorbent core, with an infrared blocking compound to block infrared light upon illumination. During manufacture of the composite article, the infrared detection system described herein could capture an image of the absorbent core containing the blocked superabsorbent polymer material and determine the concentration of superabsorbent polymer material based upon the amount of infrared light that was absorbed. A larger amount of superabsorbent material in the absorbent core would result in increased absorption.

Similar to the quantitative analysis for the amount of superabsorbent polymer material based on the absorption (or reflection) of infrared light described above, infrared blockers could also be introduced into a skin care ointment or adhesive material used on composite products and the product registered using the infrared detection system described herein. Based on the amount of absorption (or reflectance) of infrared light, the concentration of ointment or adhesive material could be determined in a manner similar to that described above for superabsorbent polymer material. The image can also provide information about the distribution or application pattern of such components.

With further reference to FIG. 2, the image analyzer 208 may be, for example, a programmable digital computer, and the comparator 210 may be implemented in a variety of hardware and software configurations. Additionally, these various components of the system 200 may be implemented singly or in combination without departing from the scope of the invention. For example, the comparator 210 and the image analyzer 208 may be implemented within a single programmable computer. It should also be understood that in any given embodiment of the invention, the combination of infrared radiation source (including its intensity and wavelength(s)), infrared detector, radiation source/detector geometry, detector filter (if any), and infrared markers (if any) can be selected as necessary to enhance detection of components of interest in a composite article.

FIG. 4 illustrates another exemplary system 400 for implementing various aspects of the present invention, including the process 100 of FIG. 1. The system of FIG. 4 is largely the same as that of FIG. 2, except that the radiation source 202 of FIG. 2 has been replaced with two radiation sources 402, 403 positioned adjacent the infrared detector on opposite sides thereof, and on a same side of the composite article as the infrared detector. Thus, the system of FIG. 4 irradiates the composite article from a top side thereof, and produces an image from infrared radiation 406 received by the detector from the top side of the composite article (some of which may be reflected from intermediate or lower components of the composite article). This is in contrast to, e.g., irradiating the backside of the composite article with infrared radiation and producing an image from infrared radiation which passes entirely therethrough, as in one embodiment of the system of FIG. 2 described above.

From the above description, it should be apparent that the present invention can be used to determine, among other things, whether one or more components are properly positioned in a wide array of composite articles. In fact, to the extent that such components do not inherently provide an infrared response which readily permits their detection using incident infrared (or other) radiation and infrared detectors, such components can be provided with a suitable infrared marker so as to impart them with a desired response, as noted above.

While suited for a wide variety of applications, the present invention is particularly useful in the production of absorbent articles, such as disposable diapers, training pants, incontinence devices, sanitary napkins, and the like. Thus, one exemplary application of the invention for detecting component positions will now be described with reference to the disposable training pant 500 illustrated in FIG. 5, and with further reference to the exemplary detection system 200 of FIG. 2. Exemplary systems and processes for producing the training pant 500 are described in international application PCT/US01/15803, the disclosure of which is incorporated herein by reference.

Figure 5:
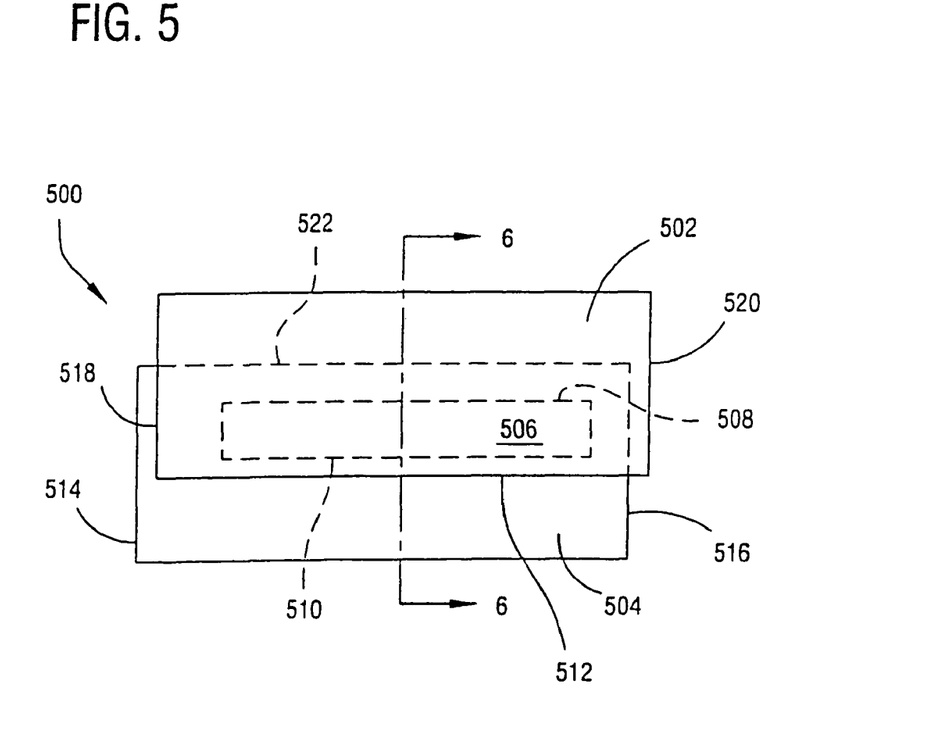
FIG. 5 is a top view of an exemplary disposable training pant having overlapping side panels.

In particular, FIG. 5 illustrates one end of a first side panel 502 of the training pant 500 joined with one end of a second side panel 504 via a fastener component 506 (shown in phantom) previously bonded to the second side panel 504, and now disposed between the two side panels, with the first side panel 502 overlapping the second side panel 504 and the fastener component 506. In this particular embodiment, the first side panel 502 and the second side panel 504 are each formed from a pigmented nonwoven material, such as a stretch bonded laminate (SBL), and the fastener component 506 is one of a hook component and a loop component of a hook-and-loop fastener (e.g., a VELCRO brand fastener available from Velcro Industries B.V.). A complementary fastener component (not shown) is also bonded to an underside of the first panel 502, and mates with the fastener component 506 bonded to the second side panel 504. Alternatively, other types of fasteners, including similar-surface interlocking fasteners, may be used.

Figure 6:
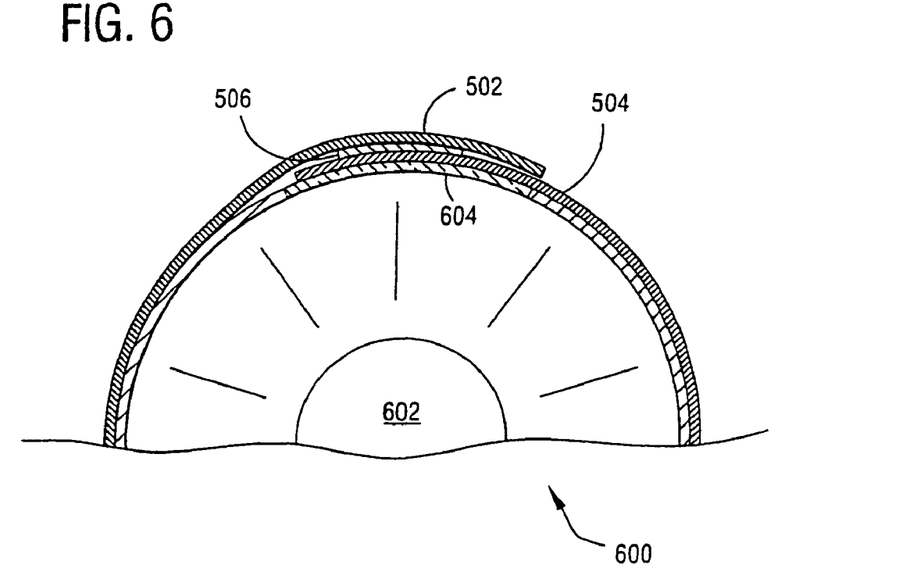
FIG. 6 is a sectional view taken along line 6-6 of FIG. 5, illustrating the training pant of FIG. 5 positioned over an infrared radiation apparatus.

The portion of the training pant illustrated in FIG. 5 is supported by an infrared radiation apparatus 600, as shown in FIG. 6. The apparatus 600 includes an infrared radiation source 602 and a diffuser 604. The diffuser 604 supports a bottom side of the training pant 500, and renders more uniform infrared radiation emanating from the infrared radiation source 602. In this example, the radiation source 602 corresponds to the radiation source 202 of FIG. 2, and the training pant 500 corresponds to the composite article 204. While only the upper component of the infrared radiation apparatus 600 is illustrated in FIG. 6, the apparatus 600 includes an equivalent lower component for irradiating an opposite side of the training pant 500 also not shown (to permit infrared detection of the training pant's opposite side using another or augmented system of the type shown in FIG. 2). In one embodiment, the infrared radiation source 602 emits infrared radiation intermittently, and the infrared detector 205 is synchronized with the radiation source 602 so as to produce an image 700 of the training pant while it is irradiated with infrared radiation.

Figure 7:
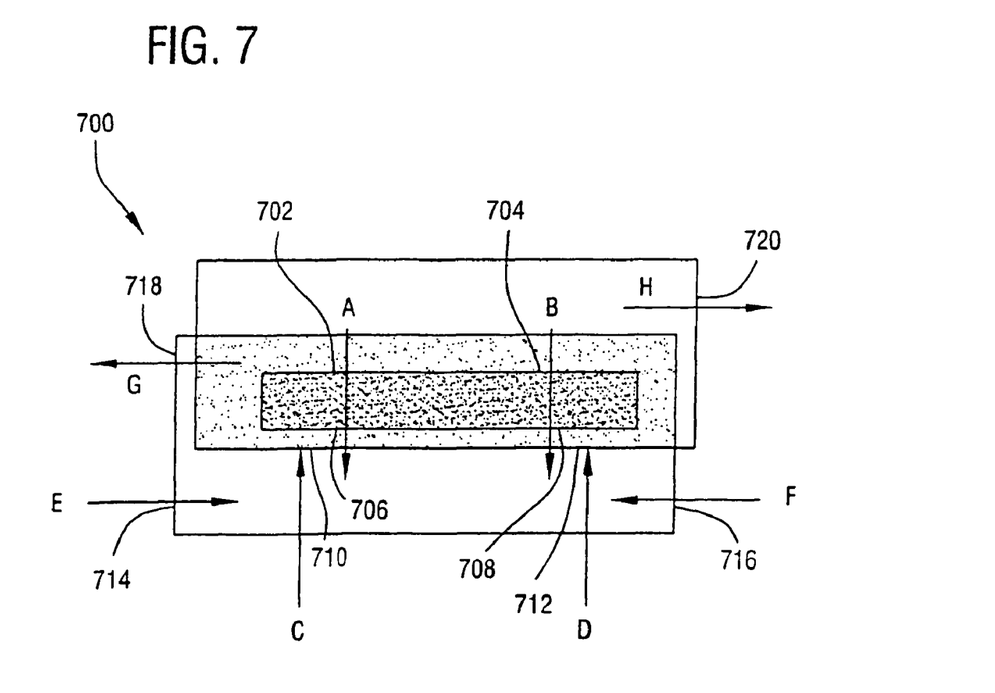
FIG. 7 illustrates an image of the training pant of FIG. 5 produced using the system of FIG. 2.

FIG. 7 illustrates the image 700 produced by the infrared detector 205 of FIG. 2 from infrared radiation emanating from a top side of the training pant 500. Note that a least amount of radiation will emanate from that portion of the first side panel 502 which overlies the fastener component 506, since such radiation (if any) must pass through the second side panel 504, the fastener component 506, and the first side panel 502, each of which at least partially inhibits infrared radiation from passing therethrough (e.g., by absorbing or reflecting such radiation). For this reason, the fastener component 506 appears in the image 700 as a dark contrast region. A medium contrast region in the image 700 corresponds to portions of the training pant where the first side panel overlies the second side panel, but not the fastener component. Light contrast regions in the image 700 correspond to portions of the training pant where the first side panel does not overlie the second side panel. Thus, it should be apparent that variations in the image 700 (which, in this implementation, are contrast or grayscale variations) correspond to edge positions of the various components. Although only three contrast regions are shown in FIG. 7, it should be understood that more or less contrast regions can be used in any given application of the invention.

Also illustrated in FIG. 7 are several arrows A-H which represent software "tools" employed by one preferred image analyzer 208 of FIG. 2 for detecting variations in the image 700 which represent edge positions of the first side panel 502, the second side panel 504, and the fastener component 506. For example, tools A and B analyze the image 700 in the directions shown to first detect contrast variations 702, 704 which correspond to positions of the fastener component's edge 508, and then detect contrast variations 706, 708 which correspond to the fastener component's edge 510. Similarly, tools C and D analyze the image 700 to detect contrast variations 710, 712 which correspond to positions of the first side panel's edge 512, tools E and F analyze the image 700 to detect contrast variations 714, 716 which correspond to positions of the second side panel's edges 514, 516, and tools G and H analyze the image 700 to detect variations 718, 720 which correspond to positions of the first side panel's edges 518, 520. Once identified by the image analyzer, the comparator of FIG. 2 compares these edge positions with predetermined position data to thereby determine whether the first side panel, the second side panel, and the fastener component are properly positioned in the training pant 500 in a fixed sense and/or relative to one another.

Note that in the particular implementation described immediately above, the fastener component 506 includes an infrared marker to increase an infrared absorption characteristic of the fastener component 506, and thereby render it more susceptible to detection in the image 700. Alternatively, the intensity of the infrared radiation source may be increased. However, a greater radiation intensity may render detection of the first side panel's edge 512 more difficult. Thus, through use of an infrared marker, in addition to appropriate selection of the infrared radiation source (including its intensity and wavelength range), the infrared detector, and the radiation source/detector geometry, a system can be devised to readily detect a wide variety of composite article components, regardless of their position. In fact, the system 200 can also be configured to detect positions of the second side panel's edge 522 which underlies the first side panel, the second fastener component (not shown) noted above, and any other component of interest.

In one embodiment, incident radiation in the range of about 700-1200 nanometers is preferred. This is because many existing inspection systems (previously used only for detecting visible and/or ultraviolet radiation) can detect wavelengths of up to about 1200 nanometers, and can thus be readily configured for implemented certain teachings of the present invention. Further, the inventors have determined that infrared radiation having a wavelength of about 940 nanometers is especially well suited for penetrating and detecting positions of pigmented nonwoven materials, including the blue and pink stretch bonded laminates commonly employed in fabricating disposable diapers, training pants, and the like. Thus, the radiation source 602 shown in FIG. 6 preferably emits radiation having a wavelength of about 940 nanometers (e.g., a commercially available infrared LED having a nominal value of 940 nanometers). Additionally, the infrared detector used in the implementation described above with references to FIGS. 5-7 preferably includes a filter for removing (i.e., blocking) radiation, such as ambient and/or scattered radiation, having a wavelength of or below about 830 nanometers (e.g., a high pass filter having a nominal value of about 830 nanometers) including visible and ultraviolet radiation. Alternatively (or additionally), one or more shrouds may be employed around the infrared detector to shield the detector from, e.g., extraneous radiation sources (such as ceiling lights, natural light, etc.).

With further reference to FIG. 2, it should be apparent that the system 200 shown therein is capable of detecting positions of not only stacked components, but also overlapping components as well as nonoverlapping adjacent components. Further, the radiation source 202 need not be an infrared radiation source in every application of the invention and, in fact, is preferably not an infrared radiation source in certain embodiments, including one or more (but not all) embodiments where a component to be detected fluoresces in the infrared spectrum in response to incident radiation outside of the infrared spectrum. The radiation source may also emit multiple wavelengths or bands of wavelengths so as to cause multiple components which respond to different wavelengths of incident radiation (due to use of infrared markers or otherwise) to exhibit their responses simultaneously, thus permitting their simultaneous detection. In this regard, the infrared detector may include only a single infrared sensor or array of sensors capable of detecting multiple wavelengths or wavelength ranges, and thus multiple components which exhibit different infrared responses to incident radiation. Alternatively, the infrared detector may include multiple and distinct infrared detectors, such as infrared cameras, and each of these detectors may be configured (via filters or otherwise) to detect distinct wavelengths or wavelength ranges. Of course, multiple systems of the types described herein may also be advantageously used in combination in any given application of the invention.

Additionally, a set of two or more discrete infrared detectors at optimized observation angles can be configured with different band pass filters, illumination sources, and detection systems enabling simultaneous real-time detection of different product components. Such an approach may advantageously yield true z-directional spatial discrimination, in addition to two-dimensional (i.e., x and y) spatial discrimination. Thus, the individual detectors can be used to detect, for example, individual components each exhibiting a different infrared response to incident radiation (through use of infrared markers or otherwise) providing detailed x,y,z spatial detection and registration of composite article components. A single infrared detector with multiple wavelength capabilities can also be used to detect different components exhibiting infrared responses at different wavelengths providing detailed x and y spatial detection. A combination of these systems can provide optimum sensing for, among other things, registration detection based upon the number of components requiring registration, the z-dimensional discrimination requirements, and cost concerns.

While one aspect of the invention, detecting a position of a component in a composite article, has been described above, another aspect of the invention includes detecting the presence (and thus the absence, when applicable) of a particular component in a composite article. For example, one exemplary process includes irradiating a composite article with radiation as the composite article moves relative to an infrared detector. A component of the composite article, when present, is known to exhibit a predefined response in response to incident radiation. Thus, the process further includes detecting the predefined response of the component in infrared radiation received from the irradiated composite article to thereby detect the presence of the component. As should be apparent, when the particular component is present in the irradiated composite article, it will alter the article's response to the infrared irradiation, such as by absorbing or reflecting infrared radiation at one or more particular wavelengths, or by fluorescing at one or more particular wavelengths. Thus, one or more variations will occur in the detected infrared radiation (such as wavelength or intensity variations) which are indicative of the component's presence. In one embodiment, a single infrared sensor element is used as the infrared detector to detect the infrared radiation received from the irradiated product as the product moves relative to the sensor element, where a high detector output level indicates a presence of the component and a low detector output level indicates an absence of the component (or vice versa).

The infrared detector may also produce an image from infrared radiation received from the irradiated composite article. In such a case, the process would include identifying the predefined response of the component in the produced image (e.g., by detecting variations, such as contrast variations, indicative of the component's presence) to thereby detect the presence of that component.

While an exemplary process for detecting a presence of a single component has been described above, it should be readily apparent that more than one and in fact many different components may be similarly detected, including components which include infrared markers for the purpose of providing or enhancing their infrared responses to incident radiation.

According to another aspect of the invention, the distribution of a plurality of components, each having a predefined response to incident radiation (due to use of infrared markers or otherwise), in a composite article may be readily determined. One exemplary process includes irradiating the composite article with the incident radiation, and producing an image from infrared radiation received from the composite article, where the image includes a pattern, formed by the predefined response of the composite articles, which corresponds to their distribution. This pattern is then compared to reference data (such as one or more predefined patterns corresponding to ideal or acceptable distributions) to determine whether the composite articles are properly distributed in the composite article. In one embodiment, the comparing includes performing a pattern matching function using a suitably configured computer device. This aspect of the invention is particularly useful in, for example, determining the distribution of absorbent particles, adhesives, and ointments used in fabrication of a disposable absorbent article.

The distribution of components in a composite article, each having a predefined response to incident radiation, may also be determined by irradiating the composite article with incident radiation, measuring a level of infrared radiation received from each of a plurality of regions of the irradiated composite article, and comparing the level of infrared radiation measured for each of the plurality of regions with reference data to thereby determine whether the components are properly distributed in the composite article. One or more infrared detectors may be provided for measuring the infrared radiation received from each region of the composite article. In one embodiment, an infrared detector is used to produce a two dimensional image from infrared radiation received from the composite article. The image is then analyzed to identify therein the regions of the composite article mentioned above, and to determine the grayscale level of each region. Thus, if the composite article is irradiated with infrared radiation, and the components of the composite article each inhibit at least some infrared light from passing therethrough, then darker portions of the produced image will correspond to regions of the composite article where relatively more of the components are present. Thus, by comparing the determined grayscale levels with reference data, the distribution of the components in the composite article may be readily determined or approximated. In one application, this process is used to determine whether superabsorbent particles are properly distributed in a disposable absorbent product, such as a diaper.

In a similar application of the present invention, the concentration (i.e., quantity) of a plurality of components, each having a predefined response to incident radiation (due to use of infrared markers or otherwise), in a composite article may be readily determined. One exemplary process includes irradiating the composite article with the incident radiation, and then measuring the predefined response of the plurality of components (e.g., the intensity of infrared radiation received from the irradiated component, such as the intensity at one or more particular wavelengths). The measured response is then compared with reference data to determine or at least approximate the quantity of the components in the composite article. This aspect of the invention is also useful in, for example, determining the quantity of absorbent particles, adhesives, and ointments used in fabricating a disposable absorbent article.

As used herein, "infrared radiation source" refers to any device capable of emitting radiation in the infrared spectrum (i.e., radiation having a wavelength between about 700 nanometers and one millimeter), regardless of whether it also emits radiation in other spectrums. Some examples of infrared radiation sources suitable for certain embodiments of the present invention include infrared LEDs, mercury vapor lamps, argon lamps, arc lamps, lasers, etc. In contrast, "radiation source" refers to any device capable of emitting radiation in any spectrum, which may or may not include the infrared spectrum.

"Infrared detector" refers to any device having one or more sensor elements (including a matrix of sensor elements) capable of sensing infrared radiation, regardless of whether such device can also sense radiation in other spectrums. Thus included in this definition are existing vision inspection cameras which are capable of detecting not only visible and ultraviolet light, but also infrared radiation of wavelengths up to about 1200 nanometers (as noted above), line scan cameras capable of building an image one line at a time from infrared radiation received from an article as the article is moved relative thereto, as well as any other device capable of producing a one, two or three dimensional image from received infrared radiation including, without limitation, a charge coupled device ("CCD").

As alluded to above, any infrared detector used in the present invention (as well as any composite article to be detected thereby) may be provided with a filter for filtering unwanted wavelengths, including those in the infrared and/or other spectrums, as desired. Such filters include low-pass filters which remove radiation above a predefined wavelength, high-pass filters which remove radiation below a predefined wavelength, band-pass filters which remove all radiation except that having a wavelength within a predefined range, and combinations thereof. One or more of these filters may be useful for removing ambient, scattered, or even incident radiation (such as when detecting components which fluoresce at different wavelengths than the incident radiation) in any given application of the invention.

The infrared and other radiation sources described herein, as well as the infrared detectors, may include fiber optic devices in various applications of the invention, such as to precisely irradiate or detect radiation from a specific component or region in a composite article.

Additionally, it should be understood that as used herein, the term "component" shall include not only discrete objects, but also objects yet to be formed into discrete objects (e.g., objects yet to be severed into discrete objects from a continuous sheet or web of material), particles (e.g., superabsorbent particles or polymers), adhesives, lotions, ointments, and other substances, as well as portions or characteristics of any such components including, for example, fold lines, bond lines (e.g., ultrasonic bond lines), bonded or adhered regions, and registration marks applied to or about components for subsequent detection during a manufacturing or inspection process. Indeed, the teachings of the invention can be used to detect the presence, position, concentration, and distribution of chemical, physical, optical, and component structural properties for any composite article under observation.

When introducing elements or features of the present invention or the preferred embodiments thereof, the articles "a", "an", "the" and "said" are intended to mean that there are one or more such elements or features. The terms "comprising", "including" and "having" are intended to be inclusive and mean there may be additional elements or features other than those listed.

As various changes could be made in the above embodiments without departing from the scope of the invention, it is intended that all matter contained in the above description or shown in the accompanying drawings shall be interpreted as illustrative and not in a limiting sense.

What is claimed is:

1. A process for preparing a component for use in a composite disposable absorbent article, the process comprising:
    selecting an infrared blocker; and
    introducing the selected infrared blocker into or onto the component to enable detection of the component when the composite disposable absorbent article is subjected to an infrared inspection system, wherein the infrared inspection system includes an infrared radiation source transmitting infrared radiation through a diffuser supporting a bottom side of the composite disposable absorbent article, and through the composite disposable absorbent article to an infrared detector.

2. The process as set forth in claim 1 wherein the infrared blocker is an absorption infrared blocker that has an absorption peak maximum in at least one of the following ranges: from about 750 nm to about 1200 nm; from about 750 nm to about 1150 nm; and from about 775 nm to about 1050 nm.

3. The process as set forth in claim 1 wherein the infrared blocker is an absorption infrared blocker that has an extinction coefficient in at least one of the following ranges: from about 1×10⁴ L/mol cm to about 5×10⁵ L/mol cm; and from about 5×10⁴ L/mol cm to about 3×10⁵ L/mol cm.

4. The process as set forth in claim 1 wherein the infrared blocker is an absorption infrared blocker that is selected from the group consisting of water soluble absorption infrared blockers, solvent soluble infrared blockers, and metal complex absorption infrared blockers.

5. The process as set forth in claim 1 wherein the infrared blocker is an absorption infrared blocker having the chemical formula:

or wherein x is a whole number from 30 to 70, y is a whole number from 32 to 112, z is a whole number from 0 to 6, R1 is selected from the group consisting of Cl, O, and Sb, wherein w and v are whole numbers from 1 to 12, R2 is I or O when R1 is Cl, S when R1 is O, and F when R1 is Sb, and R3 is selected from the group consisting of F and S.

6. The process as set forth in claim 1 wherein the infrared blocker is an absorption infrared blocker selected from the group consisting of C32H36ClN2I, C32H36Cl2N2O4, C44H60ClN2I, C36H44ClN2I, C36H44Cl2N2O4, C31H34Cl2N2O4, C34H40N2O6Cl2, C54H54N2O45, C35H42ClN2I, C35H42Cl2N2O4, C31H34Cl2N2O4, C37H42F3ClN2O2, C40H40ClN2I, C42H44ClN2I, C52H64ClN2I, C59H71Cl2N25O3, C53H52N2O3S2, C47H47ClN2O3S, C46H45ClN2O3S, C37H35ClN2O3S, C36H40ClN2I, C62H96N6SbF6, C36H40Cl2N2O4, C55H54ClO6, C47H39ClO6, C49H42ClO6, C62H92N6Sb2F12, C62H92N6Sb2F12, C52H44Cl2O6, C38H46ClN2O6S2Na, C43H47N2O6S2Na, C44H52N3O6S3Na, C36H44ClN2O6S2Na, C42H49N2O6S3Na, C46H51ClN2O6S2Na, C45H48ClN2O6S2Na, C28H40Cl4NS4Ni, C28H38Cl6NS4Ni, C32H28S4Ni, C32H26O4S4Cl2Ni, C30H48NS4Ni, C32H28O4S4Ni, and C32H30N2S4Ni.

7. The process as set forth in claim 1 wherein the infrared blocker is an absorption infrared blocker having a molecular weight in at least one of the following ranges: from about 450 g/mol to about 1450 g/mol; and from about 600 g/mol to about 825 g/mol.

8. The process as set forth in claim 1 wherein at least about 10 parts per billion of the infrared blocker is added to the component, or wherein at least about 10 parts per million of the infrared blocker is added to the component.

9. The process as set forth in claim 1 wherein the component comprises one or more of the following: a support layer, an absorbent pad, an elastic component, a fastener component, a side panel, an adhesive, a surge material, a superabsorbent polymer material, an ink for graphics, a non-woven sheet used as an outer cover or liner, and a skin care ointment.

10. The process as set forth in claim 9 wherein the infrared blocker comprises a compound which absorbs infrared radiation, and wherein the component underlies at least a portion of a second component of the composite disposable absorbent article.

11. The process as set forth in claim 1 wherein the infrared blocker is selected based on a stability of the infrared blocker at extrusion temperatures.

12. The process as set forth in claim 1 wherein the infrared blocker is introduced into or onto the component by:
    introducing the infrared blocker directly into a polymer;
    mixing the infrared blocker with the polymer to create a mixture; and
    molding or extruding the mixture to produce the component.

13. The process as set forth in claim 1 wherein the infrared blocker is introduced into or onto the component by:
    dissolving the infrared blocker into a solvent to create a solution;
    introducing the solution into a polymer; and
    molding or extruding the polymer to produce the component.

14. The process as set forth in claim 1 wherein the infrared blocker is introduced into or onto the component by:
    combining the infrared blocker with a carrier resin to create a combination;
    heating the combination to create a molten solution; and
    applying the molten solution directly to the component.

15. The process as set forth in claim 1 wherein the infrared blocker is introduced into or onto the component by:
    blending the infrared blocker into a printable ink; and
    printing a pattern of the printable ink onto a polymer film of the component.

16. The process as set forth in claim 1 wherein the infrared blocker comprises a particle light scattering compound.

17. The process as set forth in claim 1 wherein the infrared blocker comprises a compound which reflects radiation having a wavelength from about 690 nm to about 1200 nm.

* * * * *